(12) United States Patent
Nili

(10) Patent No.: US 11,173,181 B2
(45) Date of Patent: Nov. 16, 2021

(54) CAMEL HUMP-OIL BASED HERBAL COMPOSITIONS AND METHOD OF MAKING THE SAME

(71) Applicant: Nafiseh Nili, North Vancouver (CA)

(72) Inventor: Nafiseh Nili, North Vancouver (CA)

( * ) Notice: Subject to any disclaimer, the term of this patent is extended or adjusted under 35 U.S.C. 154(b) by 49 days.

(21) Appl. No.: 16/675,455

(22) Filed: Nov. 6, 2019

(65) Prior Publication Data

US 2020/0345787 A1    Nov. 5, 2020

Related U.S. Application Data

(62) Division of application No. 13/726,287, filed on Dec. 24, 2012, now abandoned.

(51) Int. Cl.
| | | |
|---|---|---|
| *A61K 35/35* | (2015.01) | |
| *A61K 36/53* | (2006.01) | |
| *A61K 36/54* | (2006.01) | |
| *A61K 45/06* | (2006.01) | |
| *A61K 8/67* | (2006.01) | |
| *A61K 8/31* | (2006.01) | |
| *A61Q 19/00* | (2006.01) | |
| *A61K 8/92* | (2006.01) | |
| *A61Q 7/00* | (2006.01) | |
| *A61Q 5/10* | (2006.01) | |

(52) U.S. Cl.
CPC ............. *A61K 35/35* (2013.01); *A61K 8/31* (2013.01); *A61K 8/676* (2013.01); *A61K 8/678* (2013.01); *A61K 8/922* (2013.01); *A61K 8/925* (2013.01); *A61K 36/53* (2013.01); *A61K 36/54* (2013.01); *A61K 45/06* (2013.01); *A61Q 5/10* (2013.01); *A61Q 7/00* (2013.01); *A61Q 19/00* (2013.01); *A61Q 19/007* (2013.01)

(58) Field of Classification Search
None
See application file for complete search history.

(56) References Cited

U.S. PATENT DOCUMENTS

2014/0178487 A1* 6/2014 Nili ..................... A61Q 19/007
424/522

OTHER PUBLICATIONS

Faraz, A. et al. Production Potential of Camel and its Prospects in Pakistan. Punjab U J Zoology 28(2)89-95, 2013. (Year: 2013).*

* cited by examiner

*Primary Examiner* — Ralph J Gitomer
(74) *Attorney, Agent, or Firm* — Barry Choobin; Patent 360

(57) ABSTRACT

Camel hump oil based herbal compositions and methods for preparing the herbal compositions for the treatment of multiple diseases, such as dermatological conditions, musculoskeletal conditions, and hair conditions. A method for extracting the camel hump oil from camel hump and a method of de-odorizing the extracted camel hump. The camel hump-oil based herbal composition includes camel hump oil, an herbal oil extract, a curing agent, and additives. The camel hump oil-based composition is topically applied.

5 Claims, 7 Drawing Sheets

CAMEL HUMP-OIL BASED HERBAL COMPOSITIONS AND METHOD OF MAKING THE SAME

CROSS-REFERENCE TO RELATED APPLICATIONS

The present application is a divisional application of Ser. No. 13/726,287 filed on Dec. 24, 2012, the contents of which are incorporated by reference herein in their entirety.

BACKGROUND

Technical Field

The embodiments herein generally relate to camel hump oil-based herbal compositions for treating diseases. The embodiments herein more particularly relate camel hump oil-based herbal compositions for the treatment of diseases of skin, hair, musculoskeletal pain, and a method of preparing the compositions.

Description of the Related Art

A camel is an important domestic animal in arid and semi-arid areas. It is used as a source of meat, hair, hides, milk, and for transport. Physiologically, the camels are incredible animals, which are well adapted to the harsh conditions of their desert habitat with several adaptation mechanisms. One of the camel's adaptation mechanisms is the hump, which is a giant mound of fat on the camel's back. There are great variations in the weight of the humps ranging from 8.5 kg to 44 kg, which accounts for 5% to 13% of body weight. The hump fats are mobilizable forms of energy to ensure the needs of the camels for maintenance, production, and adaptation to the harsh desert environment. It is believed by the inventor, without being bound to theory, that the camel hump fats may also serve as anti-inflammatory and healing agents to help the animal to cope with the workload and the harsh desert conditions.

The hump fat is an edible fat that contains a wide variety of lipids. The composition of hump fat may vary depending on the distinctive characteristics of a particular animal, environmental conditions, diet, and numerous other factors. It is, nevertheless, believed that the most typical hump fat will have approximately the composition described below.

The camel hump fat contains saturated and unsaturated fatty acids that are bound to other compounds to form fatty acid containing lipids, e.g., triglycerides and phosphoglycerides. The hump fat contains considerable amounts of essential fatty acids (EFAs). The EFAs present in the hump fat include omega-3 and omega-6 fatty acids and conjugated linoleic acid (CLA) isomers.

The weight percentages of the major fatty acids in the hump fat are oleic acid (C18:1) from 24% to 42%, palmitic acid (C16:0) from 24% to 35%, stearic acid (C18:0) from 10% to 20% and myristic acid (C14:0) from 10% to 12% (. The hump fat further contains other fatty acids such as caprylic acid (C8:0), capric acid (C10:0), lauric acid (12:0), myristoleic acid (C14:1), palmitoleic acid (C16:1), arachidic acid (C20:0), gondoic acid (C20:1), erucic acid (C22:1), lignoceric acid (C24:0), nervonic acid (C24:1), CLA isomers (c9, t11-C18:2 and t10, c12-C18:2), and omega-3 and omega-6 polyunsaturated fatty acids such as linoleic acid (C18:2n-6), α-linolenic acid (C18:3n-3), γ-linolenic acid (C18:3n-6), eicosadienoic acid (C20:2n-6), eicosatrienoic acid (20:3n-3), dihomo-gamma-linolenic acid (C20:3n-6), arachidonic acid (C20:4n-6), eicosapentaenoic acid (C20:5n-3) and cervonic acid (C22:6n-3). The hump fat further contains fatty acids with an odd number of carbon atoms such as undecylic acid (C11:0), uridecylic acid (C13:0), pentadecylic acid (C15:0), pentadecenoic acid (C15:1), margaric acid (C17:0), margaroleic (C17:1) and nonadecylic acid (C19:0).

The hump fat also contains other naturally occurring compounds including small amounts of cholesterol and considerable amounts of retinol (vitamin A), vitamin E isomers (α- γ- and δ-tocopherol), and ß-carotene, the most potent precursor of retinoids.

The camel hump fat is an edible fat that has less cholesterol than the other animal fats and has a great nutritional value in meeting the need for fat in the human diet.

The terms skin conditions and skin diseases are used, almost interchangeably at times. They vary enormously from the mild conditions, which may affect only the appearance of the skin to severe diseases, which are totally incapacitating. The degree of treatment required, or even sought, varies accordingly. Skin complaints account for approximately 5% of internal medicine visits. Rash and pruritus are particularly common complaints and frequently occur together. The presence or absence of pruritus with a primary skin lesion can dramatically change the differential diagnosis. The generalized pruritus can present as the only dermatological complaint signifying an underlying systemic disorder.

Dermatology is a branch of medicine dealing with the skin and its diseases. The skin is one of the most vulnerable organs of the body. Though seldom life-threatening, skin disorders can be uncomfortable and may cause chronic disabilities. In addition, skin disorders can lead to psychological stress because of an unpleasant appearance of skin.

The skin is the largest organ of the body, which helps in defining a look and appearance of a person. Any unsightly skin appearance, such as scarring, can affect both the mental and the physical wellbeing of the person. Diseases of skin include skin growths and discoloration.

Musculoskeletal disorders (MSDs) can affect the body's muscles, joints, tendons, ligaments, and nerves. Most work-related MSDs develop over time and are caused either by the work itself or by the employees' working environment. MSDs can also occur in the patient's life outside work either through sport—tennis (elbow); music—guitar playing or a hobby—online tracing of a family tree. These external work events can be exacerbated by their profession. They can also result from the fractures sustained in an accident. Typically, MSDs affect the back, neck, shoulders, and upper limbs; less often they affect the lower limbs.

The hair related disorders include loss of hair and reduced hair growth.

There have been many compositions developed for treating dermatological conditions but none of them treats all kinds of skin diseases and conditions. Hence there is a need to develop a camel hump oil-based herbal composition that can be used for the treatment of multiple diseases.

The above-mentioned shortcomings, disadvantages and problems are addressed herein and which will be understood by reading and studying the following specification.

OBJECTIVES OF THE EMBODIMENTS

The primary object of the embodiments herein is to provide a camel hump oil-based herbal composition for the treatment of skin and other disease conditions.

Another object of the embodiments herein is to provide a camel hump oil-based herbal composition with powerful anti-inflammatory, antioxidant, anti-itching, and healing properties.

Yet another object of the embodiments herein is to provide a camel hump oil-based herbal composition for the treatment of skin diseases.

Yet another object of the embodiments herein is to provide a camel hump oil-based herbal composition for the treatment of skin ailments including dry skin, cracked heels, psoriasis, hyperkeratosis, and eczema.

Yet another object of the embodiments herein is to provide a camel hump oil hair treatment composition for the treatment of musculoskeletal diseases.

Yet another object of the embodiments herein is to provide a camel hump oil-based herbal composition for the treatment of hair ailments.

Yet another object of the embodiments herein is to provide a camel hump oil-based herbal composition that can be applied topically over the skin.

Yet another object of the embodiments herein is to provide a method for preparing a camel hump oil-based herbal compositions for the treatment of a multiple diseases.

Yet another object of the embodiments herein is to provide a method for preparing a hump oil-based herbal composition for the treatment of skin conditions.

Yet another object of the embodiments herein is to provide a method for preparing a hump oil-based herbal composition for the treatment of musculoskeletal conditions.

Yet another object of the embodiments herein is to provide a method for preparing a hump oil composition for hair treatment such as preventing hair loss and provoking hair growth.

These and other objects and advantages of the embodiments herein will become readily apparent from the following detailed description taken in conjunction with the accompanying drawings.

SUMMARY

The various embodiments herein provide hump oil-based herbal compositions for the treatment of multiple diseases. The diseases include all kinds of dermatological conditions, musculoskeletal conditions, and hair conditions. The embodiments herein also provide a method of preparing the hump oil-based herbal compositions for the treatment of multiple disease conditions. The embodiments herein also provide a method extracting camel hump oil from camel hump and a method of deodorizing the extracted camel hump.

According to one embodiment herein, a hump oil-based herbal composition comprises camel hump oil, a herbal oil extract, and a plurality of additives. The herbal oil is an extract of a herb in botanical oil. The herb is an antioxidant, anti-inflammatory, or antioxidant herb. The herb is bay leaves and thyme, the plurality of additives includes botanical oil, vitamin C, vitamin E, an analgesic agent, glycerin, an emulsifying wax, fragrance. and a preservative. The hump oil-based herbal composition is used in dermatological conditions, musculoskeletal conditions, and in the hair treatment.

According to the embodiments herein, the camel hump oil is deodorized camel hump oil. The botanical oil is selected from a group consisting of grape seed oil, canola oil, olive oil, almond oil, avocado oil, sesame oil, or a combination thereof. The emulsifying wax is present in a concentration of 10% w/w. The vitamin C is present in an amount of 1% w/w to 2% w/w. The glycerin is present in an amount of 5% w/w. The vitamin E is present in an amount of 10,000 IU/100 gr compositions. The hump oil-based herbal composition is topically applied.

According to another embodiment herein, a hump oil-based herbal composition for the treatment of dermatological conditions includes camel hump oil, herbal oil extract of bay leaves and thyme, and additives. The camel hump oil is present in an amount of 30% w/w to 55% w/w. The herbal oil extract of bay leaves and thyme is present in an amount of 5% w/w to 30% w/w. The plurality of additives includes vitamin C, vitamin E, glycerin, an emulsifying wax, a fragrance, and a preservative. The vitamin C is present in an amount of 1% w/w to 2% w/w. The vitamin E is present in an amount of 10,000 IU/100 gr composition. The glycerin is present in an amount of 5% w/w. The emulsifying wax is present in an amount of 10% w/w. The hump oil-based herbal composition is in a form of an ointment.

According to another embodiment herein, a hump oil-based herbal composition for the treatment of musculoskeletal conditions includes camel hump oil, herbal oil extract of bay leaves and thyme, and additives. The camel hump oil is present in the composition in a range of 40% w/w to 65% w/w. The herbal oil extract of bay leaves and thyme is present in an amount of 5% w/w to 30% w/w. The plurality of additives includes an analgesic agent, vitamin C, vitamin E, glycerin, an emulsifying wax, a fragrance, and a preservative. The analgesic agent is aspirin and is present in a concentration of 0.5% w/w to 2% w/w. The vitamin C is present in an amount of 1% w/w to 2% w/w. The vitamin E is present in an amount of 10,000 IU/100 gr composition. The glycerin is present in an amount of 5% w/w. The emulsifying wax is present in an amount of 10% w/w. The hump oil-based herbal composition is in a form of an ointment.

According to one embodiment herein, a hump oil hair treatment composition includes camel hump oil and botanical oil. The camel hump oil is present in a concentration of 5% w/w to 15% w/w. The botanical oil is selected from a group consisting of grape seed oil, avocado oil, almond oil, sesame oil, or a combination thereof. The botanical oil is present in a concentration of 85% w/w to 95% w/w. The hump oil hair treatment composition is in a form of a liquid.

According to another embodiment herein, a method for making a hump oil-based herbal composition includes extracting camel hump oil. The extracted camel hump oil is deodorized. An herbal oil extract is prepared. The step of extracting the camel hump oil further includes mincing camel hump. The minced camel hump is added to a container filled with water. The amount of water in the container is double an amount of the minced camel hump. The water is heated while stirring continuously until the water boils. The contents of the container are filtered through a cheesecloth-lined strainer to obtain a filtrate. The filtrate is mixed with an equal volume of cold water having a temperature of 3° C. to 4° C. A camel hump oil is collected which is formed as a solid slab on top of the water.

The step of deodorizing the camel hump oil comprises mixing the camel hump oil with water containing ground-dried bay leaves kept at a predetermined temperature to form a mixture. The ground-dried bay leaves are present in an amount of 1% w/v to 5% w/v. The predetermined temperature is 75° C. to 85° C. The mixture is agitated for a predetermined amount of time. The predetermined amount of time is 5 to 10 minutes. The mixture is filtered to obtain a filtrate. The filtrate is cooled at a temperature to solidify the hump oil. The temperature is 3° C. to 4° C. The solidified camel hump oil is collected.

The step of preparation of the herbal oil extract includes taking a botanical oil in a container. The botanical oil is selected from a group consisting of grape seed oil, canola oil, olive oil, almond oil, avocado oil, sesame oil, or a combination thereof. A predetermined amount of dried and grounded thyme and bay leaves are added to the container. The predetermined amount of thyme is 1% w/w to 5% w/w. The predetermined amount of bay leaves is 1% w/w to 5% w/w. The container is placed on a large container containing boiling water. The contents of the container are simmered and stirred for at least 10 to 15 minutes. The contents of the container are cooled to room temperature. The contents of the container are filtered.

According to another embodiment herein, the method further comprises a step of preparing a hump oil-based herbal composition for the treatment of dermatological conditions includes the steps of preparing a solution A. The solution A is prepared by a method including the steps of dissolving a predetermined amount of a vitamin C in a predetermined amount of a purified distilled water. The predetermined amount of vitamin C is 1 gr to 2 gr. The predetermined amount of purified distilled water is 25 ml. A predetermined amount of glycerin is added to the solution and stirred. The predetermined amount of the glycerin is 5 gr. solution A is heated on a low flame until the temperature of the mixture reaches 50° C. to 60° C. The method further comprises preparing a solution B.

The solution B is prepared by a method including the steps of adding a predetermined amount of the camel hump oil in a container. The predetermined amount of the camel hump oil is 30 gr to 55 gr. A predetermined amount of an herbal oil extract is added to the container. The predetermined amount of the herbal oil extract is 5 gr to 30 gr. A predetermined amount of an emulsifying wax is added. The predetermined amount of the emulsifying wax is 10 gr. The contents of the container are heated on a low flame until the temperature of the contents of the container reaches 50° C. to 60° C. The contents of the container are stirred until a uniform blend is formed.

The contents of the solution A are added to the contents of the solution B and stirred at a predetermined temperature to form a mixture C. The predetermined temperature is 50° C. to 60° C. The mixture C is mixed in an electric mixer at a speed of 1100 rpm for 20 minutes to form an ointment. A predetermined amount of a vitamin E and a predetermined amount of a Germall™ Plus preservative are added to the ointment at a predetermined temperature. The predetermined amount of the vitamin E 10,000 IU/100 gr. The predetermined amount of Germall™ Plus preservative is 0.05% w/w to 0.1% w/w. The predetermined temperature is 35° C. to 40° C. The ointment is mixed after adding vitamin E and the preservative in an electric mixer at a speed of 1300 rpm for at least 10 minutes. The hump oil-based herbal composition is used for the treatment of dermatological conditions. The dermatological conditions include eczema, psoriasis, dry skin, cracked heels, and hyperkeratosis.

According to another embodiment herein, the method further includes a step of preparing a hump oil-based herbal composition for the treatment of musculoskeletal conditions including the steps of preparing a solution D. The solution D is prepared by a method including the steps of dissolving a predetermined amount of a vitamin C and a predetermined amount of glycerin in a predetermined amount of purified distilled water. The predetermined amount of vitamin C is 1 gr to 2 gr. The predetermined amount of the glycerin is 5 gr. The predetermined amount of purified distilled water is 15 ml. A solution of an analgesic agent is prepared. The analgesic agent is aspirin. The solution of the analgesic agent is prepared by dissolving a predetermined amount of the analgesic agent in ethanol followed by filtering. The predetermined amount of aspirin is 0.5 gr to 2 gr. The prepared solution of the analgesic agent is added to the prepared solution D and stirred. The solution D is heated on a low flame until a temperature of the mixture reaches 50° C. to 60° C.

Then, a solution E is prepared. The solution E is prepared by a method including the steps of adding a predetermined amount of the camel hump oil in a container. The predetermined amount of the camel hump oil is 40 gr to 65 gr. A predetermined amount of an herbal oil extract is added to the container. The predetermined amount of the herbal oil extract is 5 gr to 30 gr. A predetermined amount of an emulsifying wax is added to the container. The predetermined amount of the emulsifying wax is 10 gr. The contents of the container are heated on a low flame until a temperature of the contents of the container reaches 50° C. to 60° C. The contents of the container are stirred until a uniform mixture E is formed.

The contents of the prepared solution D are added to the contents of the prepared solution E and stirred at a predetermined temperature to form a mixture F. The predetermined temperature is 50-60° C. The mixture F is stirred in an electric mixer at a speed of 1100 rpm for 20 minutes to form an ointment. A predetermined amount of a vitamin E and a Germall™ Plus preservative are added to the ointment at a predetermined temperature. The predetermined amount of vitamin E is 10,000 IU/100 gr. The predetermined amount of Germall™ Plus preservative is 0.05% w/w to 0.1% w/w. The predetermined temperature is 35-40° C. The ointment is mixed after the addition of the vitamin E and the preservative in an electric mixer at a speed of 1300 rpm for at least 10 minutes. The hump oil-based herbal composition is used for the treatment of musculoskeletal conditions and pain. The pain includes pain caused by a physical injury, pain caused by medical conditions, pain caused by a discomfort associated with the medical conditions, lower back pain, knee pain, hip pain, hand pain, shoulder pain, and sport pain. The musculoskeletal conditions include osteoarthritis, sore muscles, muscle cramps, and muscle spasms. The hump oil-based herbal composition may also be applied topically to domestic animals, wherein the domestic animals include dogs, cats, and horses.

According to one embodiment herein, the method further comprises a step of preparing a hump oil composition for the hair treatment including the steps of adding a predetermined amount of the hump oil in a container. The predetermined amount of the hump oil is 5% w/w to 15% w/w. A predetermined amount of a botanical oil is added to the container. The predetermined amount of the botanical oil is 85% w/w to 95% w/w. The contents of the container are heated on a low flame until a temperature of the contents of the container reaches 50-60° C. The container is removed from the low flame. The contents of the container are stirred to obtain a uniform liquid blend. The botanical oil is selected from a group consisting of grape seed oil, canola oil, olive oil, almond oil, avocado oil, sesame oil, or a combination thereof. The hump oil hair treatment composition promotes hair growth and reduces hair loss.

The embodiments herein include the methods for camel hump oil extraction and deodorization, and preparation of hump oil-based compositions for the treatment of dermatological ailments, hair loss, and musculoskeletal conditions.

The embodiments herein provide a hump oil-based herbal composition for treating dermatological conditions including dry skin, cracked heels, eczema, hyperkeratosis, and psoriasis. The skin treatment composition includes from 30% w/w to 55% w/w of hump oil, from 5% w/w to 30% of herbal oil extract, 5% w/w of glycerin, from 1% w/w to 2% w/w of vitamin C, and 10,000 IU of vitamin E per 100 gr composition.

The embodiments herein provide a hump oil hair treatment composition for promoting hair growth and reducing hair loss. The hair treatment composition includes from 5 to 15% w/w of hump oil, and from 85% w/w to 95% w/w of botanical oil.

The embodiments herein provide a hump oil-based composition for treating musculoskeletal inflammation and pain caused by medical conditions or physical injuries. The pain treatment composition includes from 40% w/w to 65% w/w of hump oil, from 5% w/w to 30% w/w of herbal oil extract, from 0.5% w/w to 2% w/w of aspirin, from 1% w/w to 2% w/w of vitamin C, 5% w/w of glycerin, and 10,000 IU of vitamin E/100 gr composition.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
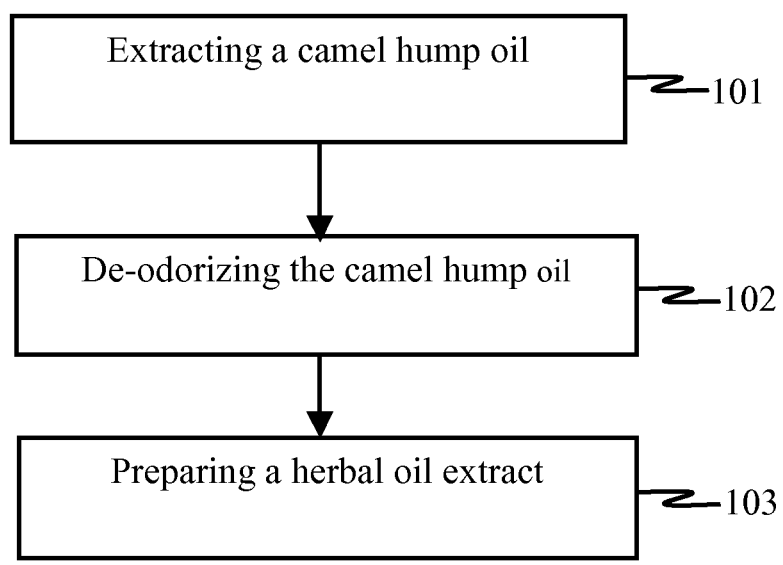
FIG. 1 illustrates a flowchart indicating the various steps involved in a method for preparing a hump oil composition, according to an embodiment herein.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical, and other changes may be made without departing from the scope of the embodiments. The following detailed description is therefore not to be taken in a limiting sense.

The various embodiments herein provide hump oil-based herbal compositions and a method of preparing the hump oil-based herbal compositions for the treatment of multiple disease conditions. The plurality of disease conditions includes dermatological conditions, musculoskeletal conditions, and a hair condition. The embodiments herein provide hump oil-based herbal compositions composed of camel hump oil in combination with herbal oil extract and excipients.

The term "hump oil" or "camel hump oil" in the specification refers to the oil derived from the camel hump fat by the described methods of extraction and deodorization. The camel hump oil is the main active ingredient of the described composition according to the embodiments herein.

The term "herbal oil extract" in the specification refers to the preparation, which is used in the embodiments herein. The herbal oil extract described herein has anti-inflammatory, antimicrobial, anti-itching, and antioxidant properties. According to the embodiments herein, the herbal oil extract helps to extend the shelf life as well as adds fragrance and therapeutic value to the finished hump oil-based herbal composition products.

The hump oil prepared herein is non irritating and non-comedogenic. The hump oil does not clog the pores of the skin and can be used in a variety of compositions including ointments, creams, and cosmetics. The hump oil can be combined with many active ingredients, which are beneficial or otherwise therapeutic. In any event, the hump oil according to the embodiments herein serves similar functions of increasing skin penetrability, moisturizing, antioxidant, anti-inflammatory, pain relieving, and healing without adverse side effects.

The natural diet of the camel consists of desert plant materials that contain a large variety of carotenoids, vitamins, terpenes, sapogenins, flavones and other naturally occurring bioactive compounds that may deposit in the fat storage depots, e.g., the hump. It is believed by the inventor, without being bound to theory, that it is the further presence of such substances within hump fat which confer upon it the potent anti-inflammatory and healing activities observed.

The camel hump oil-based compositions described herein perform a number of functions when applied topically to human skin. According to one embodiment herein, a camel hump oil-based ointment for the treatment of dermatological conditions including dry skin, cracked heels, eczema, hyperkeratosis, and psoriasis. According to a second embodiment herein, a camel hump oil-based hair treatment oil for reducing hair loss and promoting hair growth. According to a third embodiment herein, a camel hump oil-based ointment for the treatment of musculoskeletal inflammation and pain caused by medical conditions or physical injuries. The compositions according to the embodiments herein may also be applied topically to domesticated animals, such as but not limited to, dogs, cats, horses, and the like.

According to the embodiments herein, the camel hump oil-based herbal composition has powerful anti-inflammatory, anti-itch, and healing properties. The hump oil-based herbal composition is in the form of an ointment. The hump oil-based herbal composition is topically applied on the skin at affected areas. The hump oil-based herbal composition treats skin ailments including dry skin, cracked heels, psoriasis, hyperkeratosis, and eczema.

The term "hump oil" or the "camel hump oil" refers to the oil derived from camel hump using the methods provided according to the embodiments herein. The embodiments herein provide a method of extracting a camel hump oil from a camel hump and a method of deodorizing the extracted camel hump oil. The camel hump oil is in the form of a solid slab. The dermatological conditions include atrophy, blister, crust or scab, cyst, excoriation, hives or wheals, lichenification, macule, nodule or papule solid, raised bump, a patch, a pustule or a pimple, scales, and scars.

According to one embodiment herein, a camel hump oil-based herbal composition comprises a camel hump oil, an herbal oil extract, and additives. The herbal oil is an extract of an herb in a botanical oil. The herb is an anti-inflammatory, antimicrobial, antioxidant, or anti-itching herb. The herbs are bay leaves and thyme. The plurality of additives includes an emulsifying wax, vitamin C, vitamin E, botanical oil, an analgesic agent, a fragrance, and a preservative. The hump oil-based herbal composition is used in dermatological conditions, musculoskeletal conditions, and in hair treatment.

According to the embodiments herein, the camel hump oil is deodorized camel hump oil. The herbal oil extract is bay leaves and thyme extracts in a botanical oil. The botanical oil is selected from a group consisting of grape seed oil, canola oil, olive oil, almond oil, avocado oil, sesame oil, or a combination thereof.

According to another embodiment herein, a hump oil-based herbal composition for the treatment of dermatological conditions comprises a camel hump oil, an herbal oil extract of bay leaves and thyme, and additives. The camel hump oil is present in an amount of 30% w/w to 55% w/w. The herbal oil extract of bay leaves and thyme is present in an amount of 5% w/w to 30% w/w. The additive includes vitamin C, vitamin E, an emulsifying wax, glycerin, Germall™ Plus preservative, and a fragrance. The vitamin C is present in an amount of 1% w/w to 2% w/w. The vitamin E is present in an amount of 10,000 IU/100 gr. The emulsifying wax is present with an amount of 10% w/w. The glycerin is present in an amount of 5% w/w. The hump oil-based herbal composition is in a form of an ointment.

According to another embodiment herein, a hump oil-based herbal composition for the treatment of musculoskeletal conditions comprises a camel hump oil, an herbal oil extract of bay leaves and thyme, and additives. The camel hump oil is present in an amount of 40% w/w to 65% w/w. The herbal oil extract of bay leaves and thyme is present in an amount of 5% w/w to 30% w/w. The plurality of additive includes, analgesic agent, vitamin C, vitamin E, an emulsifying wax and glycerin. The analgesic agent is aspirin in a concentration of 0.5% w/w to 2% w/w. The vitamin C is present in an amount of 1% w/w to 2% w/w. The vitamin E is present in an amount of 10,000 IU/100 gr. The glycerin is present in an amount of 5% w/w. The hump oil-based herbal composition is in a form of an ointment.

According to one embodiment herein, a hump oil hair treatment composition comprises a camel hump oil and a botanical oil. The camel hump oil is present in a concentration of 5% w/w to 15% w/w. The botanical oil is selected from a group consisting of grape seed oil, avocado oil, almond oil, sesame oil, or a combination thereof. The botanical oil is present in a concentration of 85% w/w to 95% w/w, and the hump oil hair treatment composition is in a form of a liquid.

According to another embodiment herein, a method for making a hump oil-based herbal composition includes extracting camel hump oil. The extracted camel hump oil is deodorized. An herbal oil extract is prepared. The step of extracting the camel hump oil further includes mincing a camel hump. The minced camel hump is added to a container filled with an amount of water. The amount of water in the container is double an amount of the minced camel hump. The water is heated while stirring continuously until the water boils. The contents of the container are filtered through a cheese cloth-lined strainer to obtain a filtrate. The filtrate is mixed with an equal volume of cold water having a temperature of 3-4° C. A hump oil, which is formed as a solid slab on top of the water, is collected.

The step of deodorizing the camel hump oil comprises mixing the camel hump oil with water containing ground-dried bay leaves kept at a predetermined temperature to form a mixture. The grounded dried bay leaves are present in an amount of 1% w/v to 5% w/v. The predetermined temperature is 75-85° C. The mixture is agitated for a predetermined amount of time. The predetermined amount of time is 5 to 10 minutes. The mixture is filtered to obtain a filtrate. The filtrate is cooled at a temperature to solidify the hump oil. The temperature is 3-4° C. The solidified camel hump oil is collected.

The step of preparation of herbal oil extract comprises taking a botanical oil in a container. The botanical oil is selected from a group consisting of grape seed oil, canola oil, olive oil, almond oil, avocado oil, sesame oil, or a combination thereof. A predetermined amount of ground dried thyme and a predetermined amount of ground and dried bay leaves are added to the container. The predetermined amount of ground-dried thyme is 1% w/w to 5% w/w. The predetermined amount of ground and dried bay leaves is 1% w/w to 5% w/w. The container is placed on a large container containing a boiling water. The contents of the container are simmered and stirred for at least 10-15 minutes. The contents of the container are cooled to room temperature. The contents of the container are filtered.

According to another embodiment herein, the method further comprises a step of preparing a hump oil-based herbal composition for the treatment of dermatological conditions including the steps of preparing a solution A. The solution A is prepared by a method including the steps of dissolving a predetermined amount of vitamin C and a predetermined amount of glycerin in a predetermined amount of purified distilled water. The predetermined amount of Vitamin C is 1 gr to 2 gr. The predetermined amount of the glycerin is 5 gr. The predetermined amount of purified distilled water is 25 ml. The mixture is heated on a low flame and stirred until the temperature of the mixture reaches 50-60° C. The method further includes the step of preparing a solution B. The solution B is prepared by a method including the steps of adding a predetermined amount of a camel hump oil in a container. The predetermined amount of the camel hump oil is 30 gr to 55 gr. A predetermined amount of an herbal oil extract is added to the container. The predetermined amount of the herbal oil extract is 5 gr to 30 gr. A predetermined amount of an emulsifying wax is added. The predetermined amount of the emulsifying wax is 10 gr. The contents of the container are heated on a low flame until a temperature of the contents of the container reaches 50-60° C. The contents of the container are stirred until a uniform blend is formed.

The contents of the solution A are added to the contents of the solution B at a predetermined temperature to form a mixture C. The predetermined temperature is 50-60° C. The mixture C is stirred in an electric mixer at a speed of 1100 rpm for 20 minutes to form an ointment. A predetermined amount of a vitamin E and a predetermined amount of a Germall™ Plus preservative are added to the ointment at a predetermined temperature. The predetermined amount of the vitamin E is 10,000 IU/100 gr. The predetermined amount of the Germall™ Plus preservative is 0.05% w/w to 0.1% w/w. The predetermined temperature is 35-40° C. The ointment is mixed after adding the vitamin E and the preservative in an electric mixer at a speed of 1300 rpm for at least 10 minutes. The hump oil-based herbal composition is used for the treatment of dermatological conditions. The dermatological conditions include eczema, psoriasis, dry skin, cracked heels, and hyperkeratosis.

According to another embodiment herein, the method further includes a step of preparing a hump oil-based herbal composition for the treatment of musculoskeletal conditions including the steps of preparing a solution D. The solution D is prepared by a method including the steps of dissolving a predetermined amount of vitamin C and a predetermined amount of glycerin in a predetermined amount of purified distilled water. The predetermined amount of vitamin C is 1 gr to 2 gr. The predetermined amount of the glycerin is 5 gr. The predetermined amount of the purified distilled water is 15 ml. A solution of an analgesic agent is prepared. The analgesic agent is aspirin. The solution of the analgesic agent is prepared by dissolving a predetermined amount of the analgesic agent in ethanol followed by filtering. The predetermined amount of aspirin is 0.5 gr to 2 gr. The prepared solution of the analgesic agent is added to the prepared solution D. The solution D is heated on a low flame until temperature of the mixture reaches 50-60° C.

Then, a solution E is prepared. The solution E is prepared by a method comprising the steps of adding a predetermined amount of a camel hump oil in a container. The predetermined amount of the camel hump oil is 40 gr to 65 gr. A predetermined amount of an herbal oil extract is added to the container. The predetermined amount of the herbal oil extract is 5 gr to 30 gr. A predetermined amount of an emulsifying wax is added to the container. The predetermined amount of the emulsifying wax is 10 gr. The contents of the container are heated on a low flame until the temperature of the contents of the container reaches 50-60° C. The contents of the container are stirred until a uniform blend is formed.

The contents of the prepared solution D are added to the contents of the prepared solution E at a predetermined temperature to form a mixture F. The predetermined temperature is 50-60° C. The mixture F is stirred in an electric mixer at a speed of 1100 rpm for 20 minutes to form an ointment. A predetermined amount of a vitamin E and a predetermined amount of a Germall™ Plus preservative are added to the ointment at a predetermined temperature. The predetermined amount of the vitamin E is 10,000 IU/100 gr. The predetermined amount of the Germall™ Plus preservative is 0.05% w/w to 0.1% w/w. The predetermined temperature is 35-40° C. The ointment is mixed after the addition of the vitamin E and the preservative in an electric mixer at a speed of 1300 rpm for at least 10 minutes. The hump oil-based herbal composition is used for the treatment of musculoskeletal conditions and pain. The pain includes a pain caused by a physical injury, a pain caused by medical conditions, a pain caused by a discomfort associated with the medical conditions, a lower back pain, a knee pain, a hip pain, a hand pain, a shoulder pain, a sport pain. The musculoskeletal conditions include osteoarthritis, sore muscles, muscle cramps, muscle spasms. The hump oil-based herbal composition may also be applied topically to a plurality of domestic animals, wherein the plurality of domestic animals includes dogs, cats, and horses.

According to one embodiment herein, the method further includes a step of preparing a hump oil composition for hair treatment including the steps of adding a predetermined amount of a hump oil in a container. The predetermined amount of the camel hump oil is 5% w/w to 15% w/w. A predetermined amount of a botanical oil is added to the container. The predetermined amount of the botanical oil is 85% w/w % to 95% w/w. The contents of the container are heated on a low flame until the temperature of the contents of the container reaches 50-60° C. The container is removed from the low flame. The contents of the container are stirred to obtain a uniform blend. The botanical oil is selected from a group consisting of grape seed oil, canola oil, olive oil, almond oil, avocado oil, sesame oil, or a combination thereof. The hump oil hair treatment composition is for hair treatment and promotes hair growth and reduces hair loss.

FIG. 1 is a flowchart showing the various steps involved in a method for preparing a hump oil herbal composition, according to an embodiment herein. With respect to FIG. 1, camel hump oil is extracted (101). The extracted camel hump oil is deodorized (102) and an herbal oil extract is prepared (103). A hump oil-based herbal composition for the treatment of dermatological conditions is prepared (104). A hump oil-based herbal composition for the treatment of musculoskeletal conditions is prepared (105). A hump oil composition for hair treatment is prepared (106).

Figure 2:
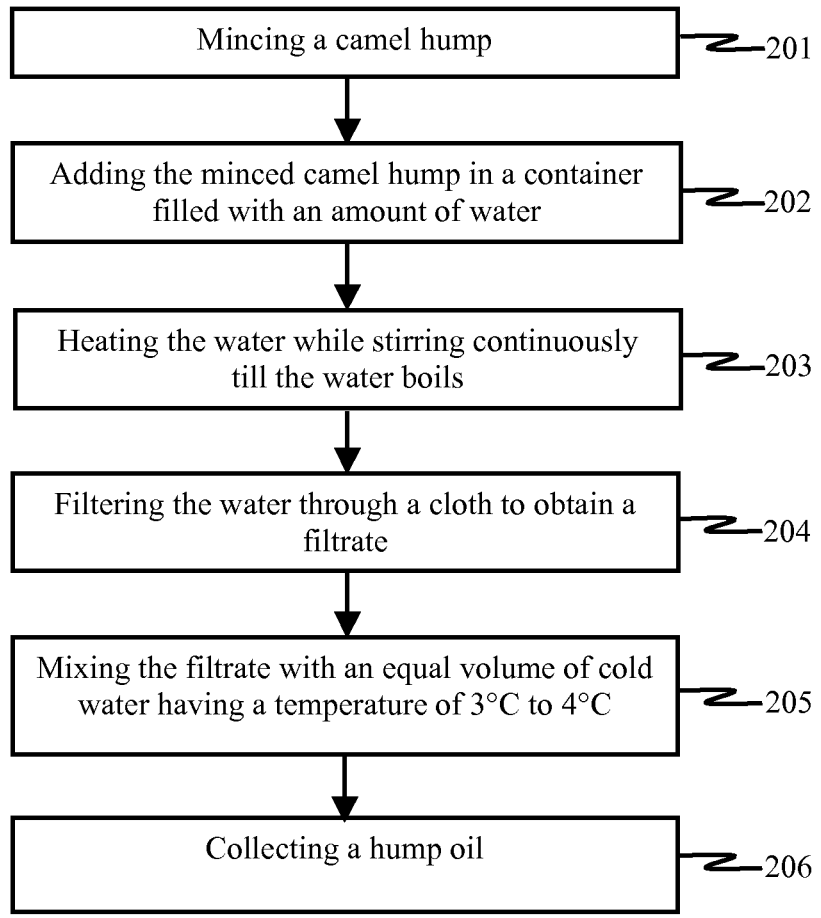
FIG. 2 illustrates a flowchart indicating the various steps involved in the step of extracting the camel hump oil, according to an embodiment herein.

FIG. 2 is a flowchart showing the various steps involved in the step of extracting the camel hump oil, according to an embodiment herein. With respect to FIG. 2, a camel hump is minced (201). The minced camel hump is added in a container filled with an amount of water (202). The amount of water in the container is double an amount of the minced camel hump. The water is heated while stirring continuously until the water boils (203). The contents of the container are filtered through a cheese cloth-lined strainer to obtain a filtrate (204). The filtrate is mixed with an equal volume of cold water having a temperature of 3-4° C. (205). A hump oil is collected (206). The hump oil is formed as a solid slab on top of the water.

Figure 3:
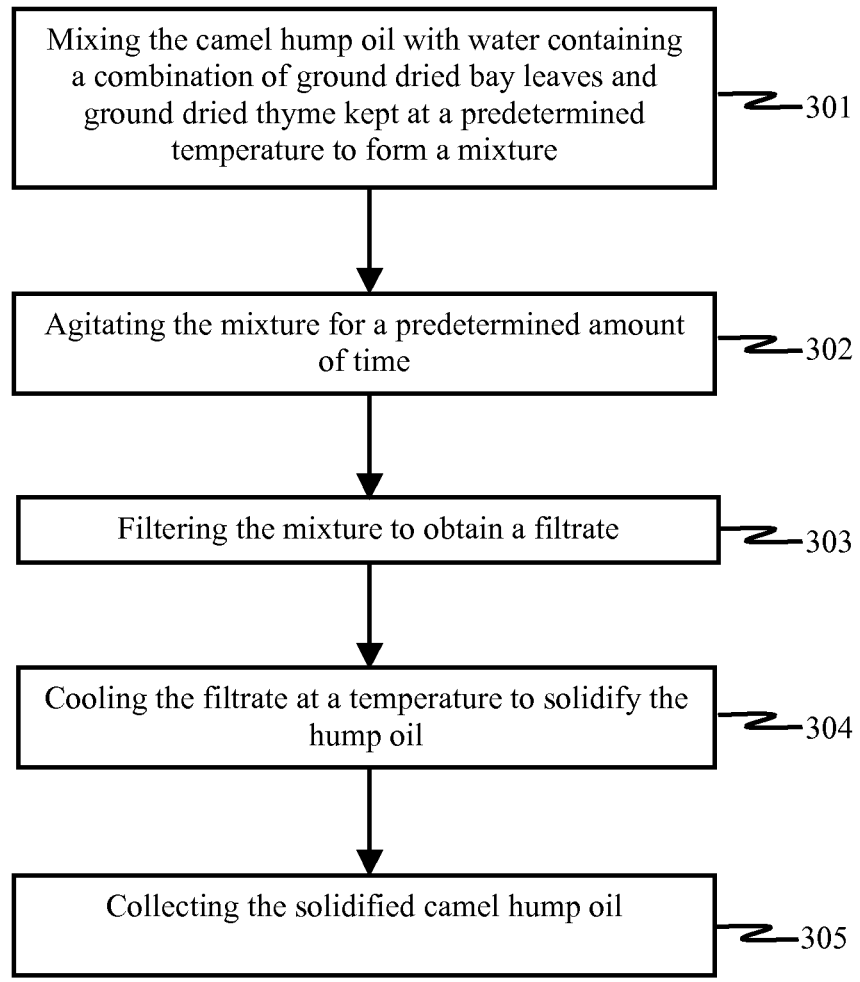
FIG. 3 illustrates a flowchart indicating the various steps involved in the step of deodorizing the camel hump oil, according to an embodiment herein.

FIG. 3 is a flowchart showing the various steps involved in the step of deodorizing the camel hump oil, according to an embodiment herein. With respect to FIG. 3, the camel hump oil is mixed with water containing dried and grounded bay leaves kept at a predetermined temperature to form a mixture (301). The dried and grounded bay leaves are present in an amount of 1% w/v to 5% w/v and the predetermined temperature is 75-85° C. The mixture is agitated for a predetermined duration (302). The predetermined duration is 5 to 10 minutes. The mixture is filtered to obtain a filtrate (303). The filtrate is cooled at a temperature to solidify the hump oil (304). The temperature is 3-4° C. The solidified camel hump oil is collected (305).

Figure 4:
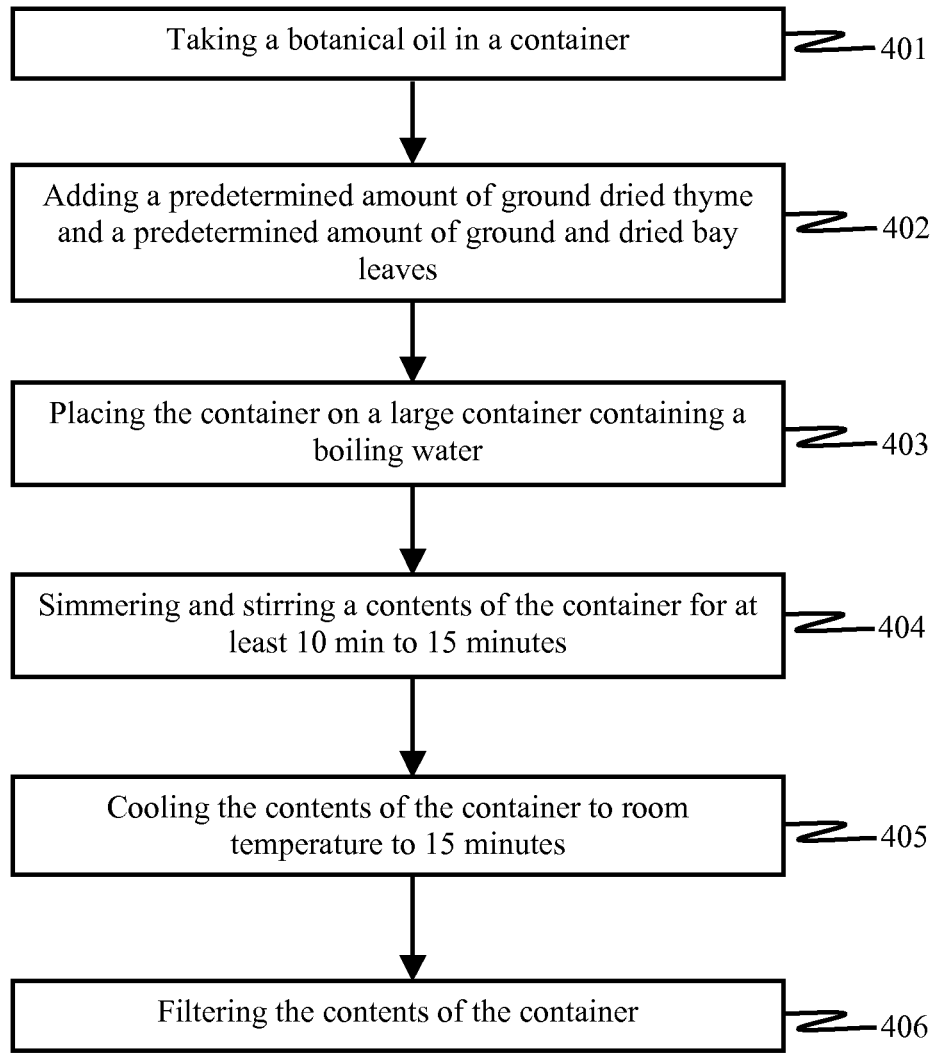
FIG. 4 illustrates a flowchart indicating the various steps involved in the step of preparing the herbal oil extract, according to an embodiment herein.

FIG. 4 is a flowchart showing the various steps involved in the step of preparation of herbal oil extract, according to an embodiment herein. With respect to FIG. 4, botanical oil is taken in a container (401). The botanical oil is selected from a group consisting of grape seed oil, canola oil, olive oil, almond oil, avocado oil, sesame oil, or a combination thereof. A predetermined amount of dried and grounded thyme and a predetermined amount of dried and grounded bay leaves are added to the container (402). The predetermined amount of dried and grounded thyme is 1% w/w to 5% w/w, and wherein the predetermined amount of dried and grounded bay leaves is 1% w/w to 5% w/w. The container is placed on a large container containing a boiling water (403). The contents of the container are simmered and stirred for at least 10-15 minutes (404). The contents of the container are cooled to room temperature (405). The contents of the container are filtered (406).

Figure 5:
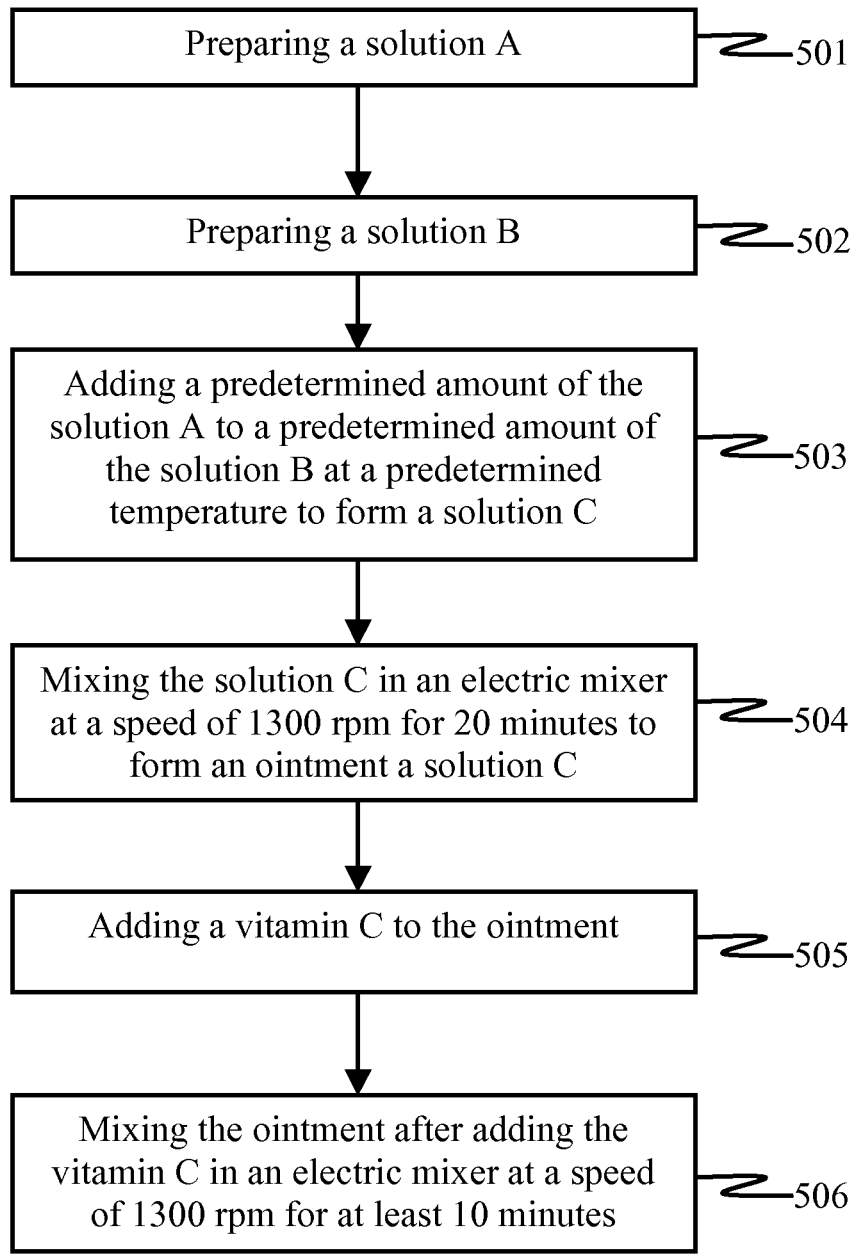
FIG. 5 illustrates a flowchart indicating the various steps involved in the method of preparing a hump oil-based herbal composition for the treatment of dermatological conditions, according to an embodiment herein.

FIG. 5 is a flowchart showing the various steps involved in the method of preparing a hump oil-based herbal combination for the treatment of dermatological conditions, according to an embodiment herein. With respect to FIG. 5, a solution A is prepared (501). The solution A is prepared by a method including the steps of dissolving a predetermined amount of vitamin C in a predetermined amount of purified distilled water. The predetermined amount of vitamin C is 1 gr to 2 gr. The predetermined amount of purified distilled water is 25 ml. A predetermined amount of glycerin is added to the solution and stirred. The predetermined amount of the glycerin is 5 gr. The solution A is heated until a temperature of the mixture reaches 50-60° C. A solution B is prepared (502). The solution B is prepared by a method including the steps of adding a predetermined amount of the camel hump oil in a container. The predetermined amount of the camel hump oil is 30 gr to 55 gr. A predetermined amount of an herbal oil extract is added to the container. The predetermined amount of the herbal oil extract is 5 gr to 30 gr. A predetermined amount of an emulsifying wax is added. The predetermined amount of the emulsifying wax is 10 gr. The contents of the container are heated on a low flame until a temperature of the contents of the container reaches 50-60° C. The contents of the container are stirred until a uniform blend is formed. The contents of the solution A are added to the contents of the solution B at a predetermined temperature to form a mixture C (503). The predetermined temperature is 50-60° C. The mixture C is stirred in an electric mixer at a speed of 1100 rpm for 20 minutes to form an ointment (504). A predetermined amount of vitamin E and a predetermined amount of a preservative are added to the ointment at a predetermined temperature (505). The predetermined amount of the vitamin E is 10,000 IU/100 gr. The predetermined amount of the preservative is 0.05% w/w to 0.1% w/w. The predetermined temperature is 35-40° C. The ointment is mixed after adding the vitamin E and the preservative in an electric mixer at a speed of 1300 rpm for at least 10 minutes (506). The hump oil-based herbal composition is used for the treatment of dermatological conditions. The dermatological conditions include eczema, psoriasis, dry skin, cracked heels, and hyperkeratosis.

Figure 6:
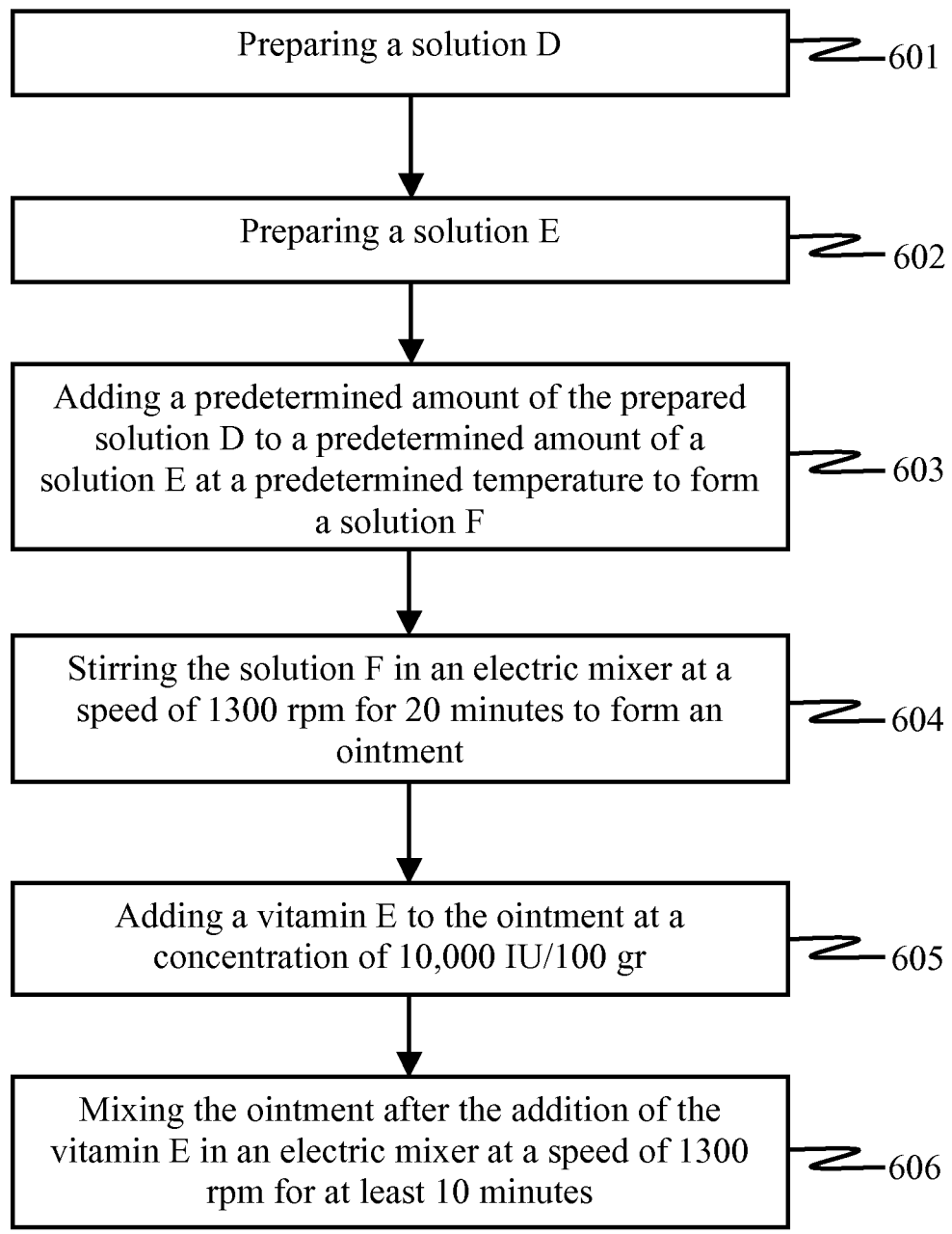
FIG. 6 illustrates a flowchart indicating the various steps involved in the method of preparing a hump oil-based herbal composition for the treatment of musculoskeletal conditions, according to an embodiment herein.

FIG. 6 is a flowchart showing the various steps involved in the preparation of an herbal composition for the treatment of musculoskeletal conditions, according to an embodiment herein. With respect to FIG. 6, a solution D is prepared (601). The solution D is prepared by a method including the steps of dissolving a predetermined amount of vitamin C in a predetermined amount of purified distilled water. The predetermined amount of vitamin C is 1 gr to 2 gr. The predetermined amount of purified distilled water is 15 ml. A predetermined amount of glycerin is added and to the solution stirred. The predetermined amount of the glycerin is 5 gr. A solution of an analgesic agent is prepared. The analgesic agent is aspirin and the solution of the analgesic agent is prepared by dissolving a predetermined amount of the analgesic agent in ethanol followed by filtering. The predetermined amount of aspirin is 0.5 gr to 2 gr. The prepared solution of the analgesic agent is added to the prepared solution D and stirred. The solution D is heated on a low flame until a temperature of the solution reaches 50-60° C. A solution E is prepared (602). The solution E is prepared by a method including the steps of adding a predetermined amount of a camel hump oil in a container. The predetermined amount of the camel hump oil is 40 gr to 65 gr. A predetermined amount of herbal oil extract is added. The predetermined amount of the herbal oil extract is 5 gr to 30 gr. A predetermined amount of an emulsifying wax is added to the container. The predetermined amount of the emulsifying wax is 10 gr. The contents of the container are heated on a low flame until the temperature of the contents of the container reaches 50-60° C. The contents of the prepared solution D are added to the contents of the prepared solution E at a predetermined temperature to form a mixture F (603). The predetermined temperature is 50-60° C. The mixture F is stirred in an electric mixer at a speed of 1100 rpm for 20 minutes to form an ointment (604). A predetermined amount of a vitamin E and a predetermined amount of a Germall™ Plus preservative are added to the ointment at a predetermined temperature (605). The predetermined amount of the vitamin E is 10,000 IU/100 gr. The predetermined amount of the preservative is 0.05% w/w to 0.1% w/w. The predetermined temperature is 35-40° C. The ointment is mixed after the addition of the vitamin E in an electric mixer at a speed of 1300 rpm for at least 10 minutes (606). The hump oil-based herbal composition is used for the treatment of musculoskeletal conditions and pain. The pain includes pain caused by physical injuries, pain caused by medical conditions, pain caused by a discomfort associated with the medical conditions, sport pain, lower back pain, knee pain, hip pain, hand pain, and shoulder pain. The musculoskeletal conditions include osteoarthritis, sore muscles, muscle cramps, and muscle spasms. The hump oil-based herbal composition may also be applied topically to domestic animals. The domestic animals include dogs, cats, and horses.

Figure 7:
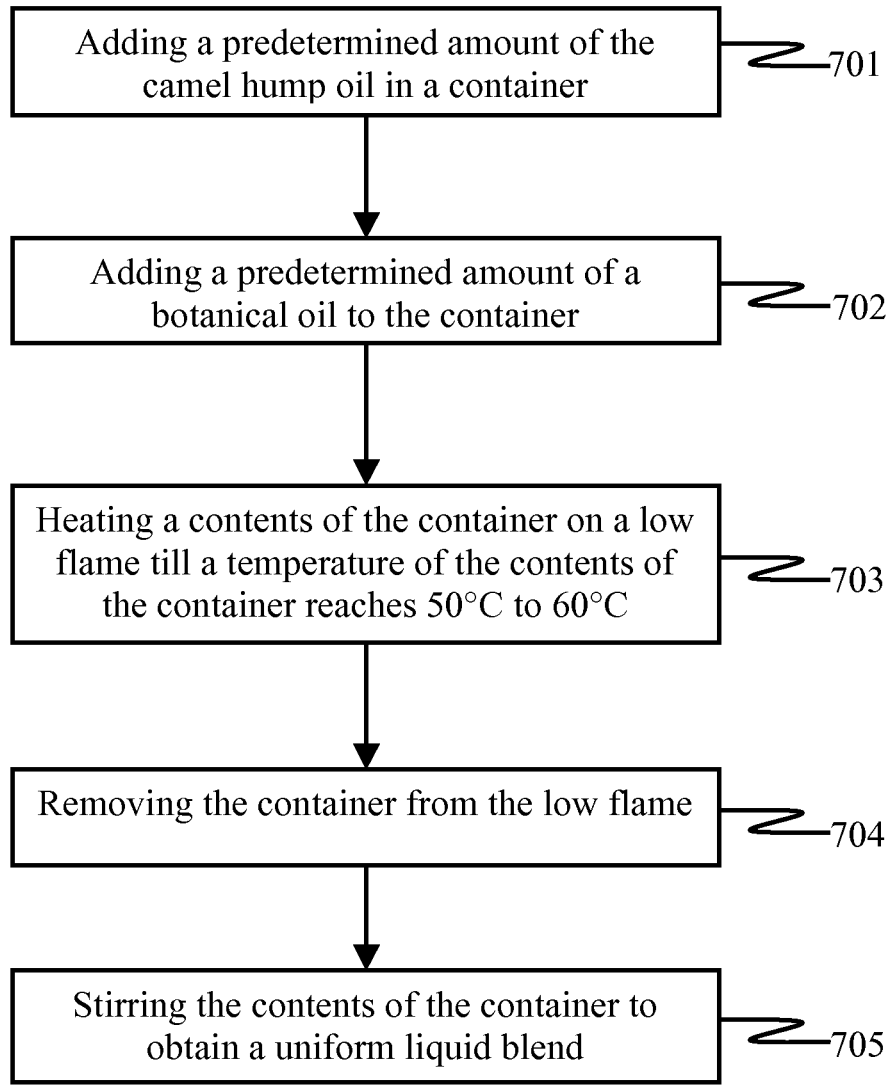
FIG. 7 illustrates a flowchart indicating the various steps involved in the method of preparing a hump oil hair treatment composition for promoting hair growth and reducing hair loss, according to an embodiment herein.

FIG. 7 is a flowchart showing the various steps involved in the method of preparation of a hump oil hair treatment composition, according to an embodiment herein. With respect to FIG. 7, a predetermined amount of the camel hump oil is added in a container (701). The predetermined amount of the camel hump oil is 5% w/w to 15% w/w. A predetermined amount of a botanical oil is added to the container (702). The predetermined amount of the botanical oil is 85% w/w to 95% w/w. The contents of the container are heated on a low flame until a temperature of the contents of the container reaches 50° C. to 60° C. (703). The container is removed from the low flame (704). The contents of the container are stirred to obtain a uniform liquid blend (705). The botanical oil is selected from a group consisting of grape seed oil, canola oil, olive oil, almond oil, avocado oil, sesame oil, or a combination thereof. The hump oil composition for hair treatment promotes hair growth and reduces hair loss.

The embodiments herein are further supported with the following examples. The examples set forth are not meant to limit the scope in any manner.

Example 1

Camel Hump Oil Extraction

Camel hump is minced and transferred into a pot containing two volumes of water. The water is brought to boil while stirring frequently until the hump fat liquefies. The heat is removed and the liquid is filtered through a cheese cloth-lined strainer. The filtrate is mixed with equal volume of cold water and cooled at 3-4° C. to separate into a slab of solidified hump oil of a deep yellowish color on the top of water containing impurities. To further remove impurities, the solidified hump oil is liquidized in two volumes of boiling water and filtered through a cheese cloth-lined strainer. The filtrate is cooled at 3-4° C. and the slab of solidified hump oil that is formed on the top of water is collected. This later process is repeated several times until hump oil of a white color is obtained. At this point, the hump oil has an unpleasant odor.

Example 2

Hump Oil Deodorization

An excellent deodorizing effect is obtained by mixing hump oil with water of 75-85° C. containing 1% w/v to 5% w/v of dried and grounded bay leaves (a potential deodorant herb) and agitating the mixture for 5 to 10 minutes followed by filtering and cooling the filtrate at 3-4° C. to solidify the hump oil. If necessary, this procedure is repeated several times. During this process, in addition to deodorization, the fat-soluble components of bay leaf are also extracted into the hump oil. These fat-soluble components have antimicrobial, antioxidant, anti-itching, and anti-inflammatory properties. By this method, hump oil of high quality is obtained without using high temperature or chemicals, which are typically used in the process of oil deodorization.

The term "hump oil" or "camel hump oil" refers to oils derived from camel hump fat by the above-mentioned methods of extraction and deodorization, and that it is the main active ingredient of the present invention.

The hump oil prepared herein is noncomedogenic, i.e., it does not clog pores of the skin. It is not irritating to skin and can be used in a variety of compositions including ointments, creams, and cosmetics. It can be combined with many active ingredients, which are beneficial or otherwise therapeutic. In any event, hump oil in any such application serves similar functions of increasing skin penetrability, moisturizing, antioxidant, anti-inflammatory, and healing without adverse effects.

Example 3

Preparation of Herbal Oil Extract

Botanical oils that may be utilized in the embodiments herein for the preparation of herbal oil extract include: grape seed oil, canola oil, olive oil, avocado oil, almond oil, sesame oil, and the like, as well as mixtures thereof. In addition, one or more oils other than the oils described herein may be included in the composition.

For preparation of herbal oil extract, the botanical oil is transferred into a small pot of a double boiler and 1% w/w to 5% w/w of ground dried thyme and 1% w/w to 5% w/w of ground dried bay leaves are added. The pot is placed on the top of the larger pot containing boiling water and simmered gently while stirring for 10 to 15 minutes, then cooled to room temperature and filtered. The herb is discarded and the filtrate is collected as the herbal oil extract.

The composition of the embodiments herein is not limited to containing the herbal oil extracts described in detail herein. Rather, the composition of the present invention may include any pain relieving, anti-inflammatory, or antioxidant type of herb known to one of ordinary skill in the art.

The term "herbal oil extract" refers to the above-mentioned preparation, which is used in the present invention. The herbal oil extract described here has, antimicrobial, anti-inflammatory, anti-itching. and antioxidant properties and will help extend shelf life as well as add fragrance and therapeutic value to the finished product.

Example 4

Other Ingredients

The hump oil-based herbal compositions described above may further comprise various additional ingredients and compounds. Examples of such additional components include a natural fragrance, such as floral or herbal fragrance without limitation. The fragrance can be omitted. It may be desirable to omit fragrance in circumstances in which the composition is intended for use on sensitive individuals or individuals who may undergo an allergic reaction to fragrance.

Example 5

Composition for the Treatment of Dermatological Conditions

One embodiment of the invention includes a hump oil-based herbal composition for treating skin ailments. As used herein, the term "ailment" refers to any item on or in the skin that would benefit from treatment, such as but not limited to, skin conditions, e.g., eczema, psoriasis, dry skin, cracked heels, and hyperkeratosis. The ointment has antimicrobial, anti-inflammatory, antioxidant, and anti-itching activities, moisturizes the skin, reduces inflammation, and relieves dryness.

The method of preparing the ointment includes the following steps:

Phase 1: In a container, 1 gr to 2 gr of vitamin C is dissolved in 25 ml of purified distilled water and 5 gr of glycerin is added. The mixture is stirred over a double boiler on low heat until temperature of the contents of the container reaches 50-60° C. and a homogeneous solution is obtained.

Phase 2: In a container, 30 gr to 55 gr of hump oil, 5 gr to 30 gr of herbal oil extract and 10 gr of emulsifying wax are combined and heated on low heat until temperature of the contents of the container reaches 50-60° C.

The concoction is stirred constantly until a uniform blend is formed.

When the contents in both containers are at the same temperature of about 50-60° C., the contents of phase 1 container are slowly added to the contents of phase 2 container and stirred with an electric mixer at 1100 rpm for 20 minutes or until the mixture cools to 35-40° C. and a uniform ointment is formed. Vitamin E (10,000 IU/100 gr ointment) and Germall™ Plus preservative (0.05% w/w to 0.1% w/w) are added to the ointment and mixed with an electric mixer at 1300 rpm for 10 minutes. The topical composition of the present invention may be formulated in any acceptable topical vehicle, including gel, white petrolatum, bee wax, etc.

The ointment of the present invention may be applied over the affected skin area twice a day or more, depending on the amount of time for which relief lasts. The treatment area is washed with mild soap and water and the skin is dried with a clean towel. The ointment may be applied to the affected area and to a portion of the area just outside of the affected area and is rubbed gently until it is absorbed into the skin.

Example 6

Composition for Hair Treatment

Embodiment of the invention further includes a hump oil-based herbal composition for promoting hair growth and reducing hair loss.

In a container, 5% w/w to 15% w/w of hump oil and 85% w/w to 95% w/w of botanical oil are combined and heated over a double boiler on low heat until temperature of the mixture reaches 50-60° C. and hump oil liquefies. The concoction is removed from heat and stirred constantly until oils mix and a uniform blend is obtained.

Botanical oils that may be utilized for the preparation of hair treatment oil include: grape seed oil, avocado oil, almond oil, sesame oil, and the like, as well as mixtures thereof In addition, one or more oils other than the oils described herein may be included in the composition.

The composition prepared as described herein above may be topically applied to the scalp, massaging the mixture through evenly for 2 to 3 minutes. The hair is wrapped in a towel for 2 to 3 hours to allow the mixture to penetrate the scalp and hair. The hair is washed with a gentle shampoo. This process should be repeated at least once a week.

Example 7

Composition for the Treatment of Musculoskeletal Conditions

Embodiment of the invention further includes a hump oil-based herbal composition for treating musculoskeletal inflammation and pain of a subject. The pain is caused by physical injuries or medical conditions, or from discomfort associated with these conditions. The ointment has analgesic, anti-inflammatory, antioxidant, and healing activities, and comprises of hump oil, herbal extracts, vitamins, and an analgesic agent. Preferred analgesic agent is aspirin. Addition of aspirin enhances the pain-relieving benefits of the ointment. The ointment may be applied topically to a subject for relief of pain, discomfort and other symptoms associated with osteoarthritis; lower back pain; sore muscles, including muscle cramps and muscle spasms; auto accident injuries; knee, hip, shoulder, and hand pain; sports injuries, strains and sprains; musculoskeletal injuries. The ointment of the present invention may also be applied topically to domesticated animals, such as but not limited to, dogs, cats, horses, and the like.

The method of preparing the ointment comprises the following steps:

Phase 1: In a container, 1 gr to 2-gr vitamin C is dissolved in 15 ml of purified distilled water and 5 gr of glycerin is added. The mixture is stirred until a homogeneous solution is obtained.

From 0.5 gr to 2 gr of aspirin is dissolved in ethanol and filtered. The filtrate is mixed with phase 1 contents and stirred over a double boiler on low heat until temperature of the contents of phase 1 container reaches 50-60° C.

Phase 2: In a container, 40 gr to 65 gr of hump oil, 5 gr to 30 gr of herbal oil extract and 10 gr of emulsifying wax are combined and heated over a double boiler on low heat until temperature of the contents of the container reaches 50-60° C. Then, the mixture is stirred until a uniform blend is formed. When the contents in both containers are at the same temperature of about 50-60° C., the contents of phase 1 container are slowly added to the contents of phase 2 container and stirred with an electric mixer at 1100 rpm for 20 minutes or until the mixture cools to 35-40° C. and a uniform ointment is formed. Vitamin E (10,000 IU/100 gr) and Germall™ Plus preservative (0.05% w/w to 0.1% w/w) are added to the ointment and mixed with an electric mixer at 1300 rpm for 10 minutes. The topical composition of the present invention may be formulated in any acceptable topical vehicle, including gel, white petrolatum, wax, etc.

Skin Ailments

The embodiments herein provide anti-inflammatory, anti-oxidant, anti-itching, antimicrobial agents, and other beneficial compounds with healing activities capable of moisturizing, normalizing, and stabilizing the skin and can be used to aid in treating skin ailments. The typical skin ailments or conditions, which may be treated with the camel hump oil-based composition, include: dry skin, cracked heels, eczema, psoriasis, psoriasis arthritis, and hyperkeratosis.

The hump oil-based skin treatment ointment described herein has anti-inflammatory, antimicrobial, antioxidant, and anti-itching qualities, do not irritate the skin, and that can be used as many times as required without adverse side effects. It performs a number of functions when applied to the skin. For example, it can replenish natural skin oils, maintain skin hydration, reduce inflammation, soothe redness, and control itching, flaking and scaling associated with many stubborn skin conditions including dry skin, cracked heels, eczema, psoriasis and hyperkeratosis.

Musculoskeletal Conditions

The non-steroidal anti-inflammatory and analgesic drugs that are often used as treatments to manage joint diseases only function to temporary relieve the pain. The present invention provides a hump oil based-pain treatment ointment for reducing inflammation of the joints and providing relief from the joint pain while being non-irritating to the skin, and that it has long-lasting healing properties without adverse effects. The ointment penetrates the skin rapidly and adequately and acts to provide effective transport across the dermis or mucous membranes of said area of pain or discomfort to provide effective relief from swelling, stiffness, and the pain and discomfort caused by a variety of inflammatory medical conditions or physical injuries. For example, the ointment assists in the relief of the effects of arthritic pain by promoting an anti-inflammatory effect to restore flexibility to stiff and painful joints. The ointment will also help maintain joint mobility and flexibility in joint overuse injury or repetitive strain injury affecting variety of worker groups like assembly workers, jackhammer operators, typists, musicians and sport players. Physical activity can subject the human body to intense strains, which may cause muscle and/or joint pain. When used on activity related injuries, the pain relief ointment of the present invention speeds recovery through reducing inflammation and restores flexibility to tight muscles or joints and thereby assists in quick recovery.

The following examples further illustrate the use of the invention for the treatment of skin ailments, hair loss and musculoskeletal conditions and are not intended to limit the same.

Example 8

A 35-year-old male that had very dry skin with some cracks on his hands applied the hump oil-based skin treatment ointment on the affected area two to three times per day. Within two days, the skin was noticeably softer, rejuvenated, hydrated, and the dry, crackly skin had smoothed out. The condition was completely cured within 4 days and the skin acquired normal tone and texture within one week.

Example 9

A 40-year-old female had cracked heels for about two years with temporary relief from steroidal creams, which have limited use. She used the hump oil-based skin treatment ointment on her heels two times per day. The ointment healed her skin significantly and improved her condition within two days. The severely broken heels were completely cured within one week. She continued to use the ointment since been healed to keep her heels healthy and hydrated.

Example 10

A 7-year-old male had severe eczema on the back of his hands and arms. The eczema had been recurring for a period of two years and causing nocturnal itching. He used the hump oil-based skin treatment ointment to the affected area two to three times per day. The itching stopped within the first hour of treatment. Within the first few days, the patches on the skin started to smooth out. After use for three weeks, the appearance of the skin had improved and acquired a normal tone and texture.

Example 11

A 25-year-old male with plaque psoriasis on his legs had difficulty controlling the psoriasis for over 10 years. The individual had been treated previously with limited success, with maximum B range ultraviolet rays (UVB), along with topically applied tar, corticosteroids, and 5-fluorouracil. He applied the hump oil-based skin treatment ointment topically to the affected area two times per day. At the end of the second week, the ointment resulted in significant clearing of the psoriatic plaques. After five weeks, the psoriatic plaques competently cleared.

Example 12

A 36-year-old female had suffered from mild psoriasis on her elbows and fingertips. She applied the hump oil-based skin treatment ointment topically to the affected area two times per day. At the end of the two weeks, the ointment resulted in significant clearing of the psoriasis and the appearance of the skin had improved and acquired a more normal tone and texture.

Example 13

A 55-year-old female had hyperkeratosis on her palm and her sole since the age of six months. She used the hump oil-based skin treatment ointment every evening at bedtime and every morning. After two weeks of this treatment regimen, she had significant improvement of her skin, including decreased hyperkeratosis, and softer and hydrated skin. The patient's skin condition remained improved with regular use of the ointment. She had used other available treatments but none of the treatments had improved her condition to this extent.

Example 14

A 45-year-old female had experienced hair loss and hair thinning on her scalp. The hump oil hair treatment composition was applied topically to the individual's scalp two times per week. After approximately two weeks of this treatment, cessation of hair thinning was observed. At approximately one month from the first application, restored hair growth in the affected areas was detected. At approximately three months from the first application, substantial growth and thickness of the individual's hair was detected.

Example 15

A 48-year-old female individual complaining of severe wrist joint pain was treated with the hump oil-based pain treatment ointment every evening at bedtime and every morning. Upon application of the ointment, the pain and discomfort was alleviated within 10 to 15 minutes. After two weeks of use, the onset of pain was less often and the individual used the ointment as required.

Example 16

A 50-year-old-male suffering from arthritis pain in his knees applied the hump oil-based pain treatment ointment every night at bedtime and every morning. The ointment rapidly alleviated pain and discomfort within 10 to 15 minutes and helped to ease out the stiffness, thereby increasing mobility and flexibility of the knee. After two weeks of use, the onset of pain and discomfort was less often and the individual used the ointment as required. Regular use of the hump oil-based pain treatment ointment decreased pain symptoms and allowed maintenance of reasonable activities.

Example 17

A 55-year-old female complaining of pain of plantar fasciitis, which is which is inflammation of the connective tissue on the sole of the foot, used the hump oil-based pain treatment ointment daily every night at bedtime. The ointment rapidly reduced inflammation and she could sleep without pain and discomfort. After one month of use, the individual did not need to use the ointment daily and only used occasionally as required.

Example 18

A 48-year-old male complaining of severe lower back and hip pain was treated with the hump oil-based pain treatment ointment, after a hot bath before bed. He felt almost immediate relieve from pain after each use and could sleep without pain. After one month of use, the onset of pain and discomfort was less often and he did not need to use the ointment on daily basis but only used occasionally as required.

The ointment prepared as described herein above may be topically applied to the area to be treated for relief from a variety of symptoms of musculoskeletal conditions. An amount of the ointment is applied to an area of discomfort and lightly rubbed over the area until the ointment is absorbed into the skin. The ointment can be used about 2 to 3 times daily or more, depending on the amount of time for which relief lasts. Relief of at least one of the symptoms, that is, pain, soreness, swelling or inflammation, typically occurs within about 10-15 minutes.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments, which as a matter of language might be said to fall there between.

I claim:

1. A method for preparing a herbal composition, the method comprising the steps of:
   mincing a camel hump;
   adding the minced camel hump in a container filled with water;
   heating the water containing the minced camel hump while stirring continuously until the water boils;
   filtering the boiled water containing the minced camel hump to obtain a filtrate;
   mixing the filtrate with cold water having a temperature in a range of 3-4° C. resulting in solidification of hump oil;
   collecting the solidified hump oil;
   mixing the hump oil with water containing dried and ground bay leaves and thyme at a predetermined temperature for a predetermined duration to obtain a mixture;
   filtering the mixture to obtain a second filtrate;
   cooling the second filtrate to solidify deodorized hump oil.

2. The method according to claim 1, wherein the method further comprises the steps of:
   adding a predetermined amount of the deodorized hump oil to a container; and
   adding a predetermined amount of an herbal oil extract to the predetermined amount of the deodorized hump oil, wherein the herbal oil extract is prepared by the steps:
      adding a predetermined amount of dried and ground thyme and bay leaves to a predetermined amount of botanical oil to obtain an herbal oil extract mixture, and
      simmering the herbal oil extract mixture to obtain the herbal oil extract.

3. The method according to claim 2, wherein the botanical oil is selected from the group consisting of grape seed oil, canola oil, an olive oil, almond oil, avocado oil, sesame oil, or a combination thereof.

4. The method according to claim 1, wherein the bay leaves are present in an amount of 1-2% w/v and the thyme is present in an amount of 1-2% w/v in the mixture.

5. The method according to claim 4, wherein in the step of mixing the hump oil with water, the predetermined temperature is 75-85° C. and the predetermined duration is 5-10 min.

* * * * *